(12) United States Patent
Corndorf

(10) Patent No.: US 8,346,190 B2
(45) Date of Patent: Jan. 1, 2013

(54) PRECOMPENSATING FOR UNDESIRED ELECTRICAL RESPONSES OF RECEIVER COMPONENTS OF AN IMPLANTABLE MEDICAL DEVICE

(75) Inventor: Eric D. Corndorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 596 days.

(21) Appl. No.: 12/550,672

(22) Filed: Aug. 31, 2009

(65) Prior Publication Data

US 2011/0054571 A1  Mar. 3, 2011

(51) Int. Cl.
*H04B 1/04* (2006.01)
(52) U.S. Cl. .................. 455/114.3; 375/296; 607/60
(58) Field of Classification Search .............. 455/39, 455/73, 114.3, 115.1, 501, 67.13, 63.1, 24, 455/423, 456.1, 126, 127.1, 295, 13.4, 12.1, 455/296, 504, 430; 375/221, 285, 296, 346, 375/297; 330/149, 107, 52, 278, 291, 136; 331/17; 348/E5.108, E5.113, 608, 723; 370/315; 359/326–328
See application file for complete search history.

(56) References Cited

U.S. PATENT DOCUMENTS

| | | | |
|---|---|---|---|
| 5,600,718 A | | 2/1997 | Dent et al. |
| 6,535,766 B1 | | 3/2003 | Thompson et al. |
| 6,949,075 B2 | | 9/2005 | Hatlesad et al. |
| 7,248,625 B2 | | 7/2007 | Chien |
| 2002/0160715 A1 | * | 10/2002 | Davis et al. .................. 455/63 |
| 2004/0001559 A1 | * | 1/2004 | Pinckley et al. .............. 375/297 |
| 2004/0138518 A1 | | 7/2004 | Rise et al. |
| 2004/0259512 A1 | * | 12/2004 | Busson et al. ............. 455/190.1 |
| 2005/0163250 A1 | | 7/2005 | McCallister |
| 2005/0165455 A1 | | 7/2005 | Schomburg et al. |
| 2005/0255814 A1 | * | 11/2005 | Song et al. ................ 455/114.3 |
| 2007/0057737 A1 | * | 3/2007 | Davis et al. .................... 331/17 |
| 2007/0153884 A1 | * | 7/2007 | Balasubramanian et al. 375/221 |
| 2007/0160715 A1 | | 7/2007 | Elnakib et al. |
| 2007/0279149 A1 | | 12/2007 | Dal Molin |
| 2009/0222065 A1 | * | 9/2009 | Dlugos et al. ................. 607/60 |

(Continued)

OTHER PUBLICATIONS

Tuthill J. et al.; "Implementation of Automatic Digital Compensation in IQ Demodulators," Telecommunications, Electronics and Networking (TEN) Research Group, Department of Electrical and Electronic Engineering, University of Western Australia, Nedlands, Australia http://195.134.67.70/eurasip/Proceedings/Eusipco/Eusipco2000/sessions/FriAm/OR4/cr1188.pdf, downloaded on Aug. 11, 2009.

(Continued)

*Primary Examiner* — Lana N Le
*Assistant Examiner* — Golam Sorowar
(74) *Attorney, Agent, or Firm* — Stephen W. Bauer; Michael J. Ostrom

(57) ABSTRACT

This disclosure describes to techniques to compensate for distortions introduced into received signals by one or more receiver components that have undesirable electrical responses, such as nonlinear phase response, sloped (or non-flat) amplitude response or both. An external device or other device with more power resources than an IMD filters signals to be transmitted to the IMD to pre-compensate for distortions introduced by the undesired electrical responses of the one or more receiver components of the IMD. In this manner, at least a portion of the burden of digital processing to compensate for undesired electrical responses of the receiver components is shifted from the IMD to the external device, which is better equipped to perform such heavy computationally complex functions.

7 Claims, 6 Drawing Sheets

U.S. PATENT DOCUMENTS

2009/0302940 A1* 12/2009 Fuller et al. .................. 330/149

OTHER PUBLICATIONS

Tuthill J. et al.; "Automatic digital pre-compensation in IQ modulators," icassp, vol. 3, pp. 1621-1624, Acoustics, Speech, and Signal Processing, 1999. Proceedings. vol. 3, 1999 IEEE International Conference on, 1999.

Du, Liang B. et al.; "Improved Nonlinearity Precompensation for Long-Haul High-Data-Rate Transmission Using Coherent Optical OFDM"; Optics Express; Nov. 2008; vol. 16, No. 24.

(PCT/US2010/031160) PCT Notification of Transmittal of the International Search Report and the Written Opinion of the International Searching Authority, Mailed Jul. 19, 2010, 9 pages.

* cited by examiner

PRECOMPENSATING FOR UNDESIRED ELECTRICAL RESPONSES OF RECEIVER COMPONENTS OF AN IMPLANTABLE MEDICAL DEVICE

TECHNICAL FIELD

The disclosure relates generally to implantable medical devices and, in particular, to precompensating for undesired electrical responses of one or more receiver components of an implantable medical device (IMD).

BACKGROUND

A wide variety of IMDs that deliver a therapy to or monitor a physiologic or biological condition of a patient, or both, have been clinically implanted or proposed for clinical implantation in patients. The IMD may deliver therapy to or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy or the like.

The IMD may exchange communications with an external device, such as a programming device or a monitoring device located in the vicinity of the patient. The information transmitted from the IMD to the external device may be information related to a condition of the patient, such as physiological signals measured by one or more sensors, or information related to a therapy delivered to the patient. This information may be previously stored or real-time information. The IMD may also receive information from the external device, such as configuration information that may be used to configure a therapy to be provided to the patient.

The IMD and the external device may exchange information using radio frequency (RF) communications. For example, the IMD and the external device may communicate in the 402-405 megahertz (MHz) frequency band in accordance with the Medical Implant Communications Service (MICS) band regulations. As another example, the IMD and the external device may communicate over the 401-402 MHz or 405-406 MHz frequency bands in accordance with the Medical External Data Service (MEDS) band regulations.

SUMMARY

This disclosure relates to techniques to compensate for distortions introduced into received signals by one or more receiver components that have undesirable electrical responses, such as nonlinear phase response, sloped (or nonflat) amplitude response or both. In accordance with the techniques described in this disclosure, a device with more power resources than the IMD filters signals to be transmitted to an IMD to pre-compensate for distortions introduced by the undesired electrical responses of the one or more receiver components of the IMD. Typically, this device will be an external device, such as a programming device or a monitoring device. In this manner, at least a portion of the burden of digital processing to compensate for undesired electrical responses of the receiver components is shifted from the IMD to the external device, which is better equipped to perform such heavy computationally complex functions, thereby reducing power consumption in the IMD. In other instances, however, the other device may be another implanted device that has sufficient power resources.

In some instances, however, digital processing to compensate for undesired electrical responses of the receiver components may be distributed between the IMD to the external device such that each of them performs a portion of the compensation. In this case, the external device performs pre-compensation and the IMD performs post-compensation to fix distortions not accounted for in the pre-compensation of the external device.

In one example, this disclosure is directed to a method comprising generating a signal for transmission to an implantable medical device, applying a pre-compensation filter to the generated signal to pre-compensate for an undesired electrical response of one or more components of a transceiver of the implantable medical device, and transmitting the pre-compensated signal to the implantable medical device.

In another example, this disclosure is directed to a medical system comprising an implantable medical device comprising at least one receiver component that has an undesired electrical response and an external device that transmits signals to the implantable medical device. The external device includes a pre-compensation filter that is applied to the signals prior to transmission of the signals to pre-compensate for at least a portion of an undesired electrical response of the at least one receiver component of the implantable medical device.

In another example, this disclosure is directed to a computer-readable medium comprising instructions that, when executed by at least one processor, cause a device to generate a signal for transmission to an implantable medical device, apply a pre-compensation filter to the generated signal to pre-compensate for an undesired electrical response of one or more components of a transceiver of the implantable medical device, and transmit the pre-compensated signal to the implantable medical device.

This summary is intended to provide an overview of the subject matter described in this disclosure. It is not intended to provide an exclusive or exhaustive explanation of the invention as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
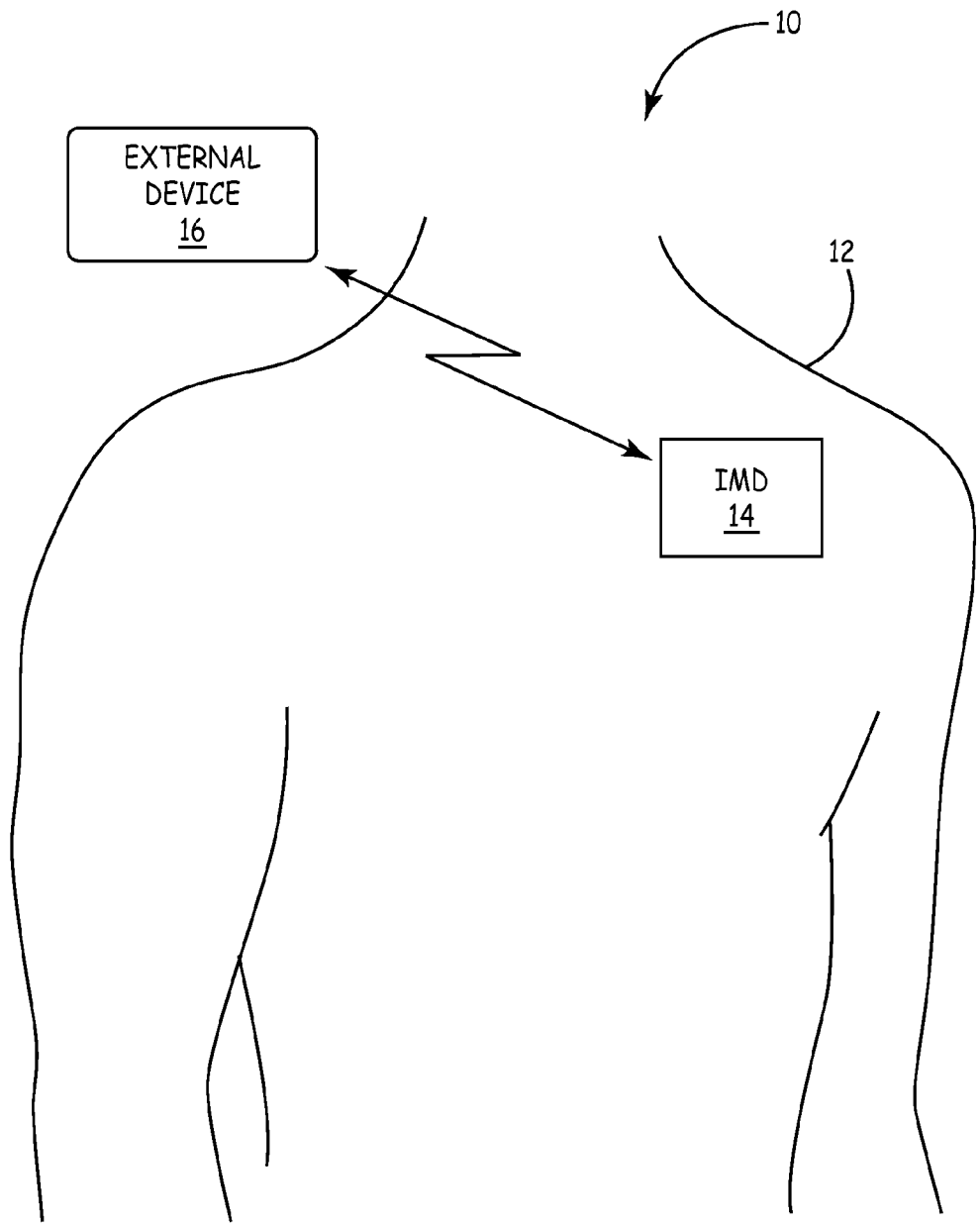
FIG. 1 is a conceptual diagram illustrating an example medical system in which an IMD and an external device use the pre-compensation techniques described in this disclosure.

FIG. 1 is a conceptual diagram illustrating an example medical system 10 in which an IMD 14 and an external device 16 use the pre-compensation techniques described in this disclosure. Although the pre-compensation techniques of this disclosure are described as being performed by external device 16, the pre-compensation may be performed by another implantable medical device with more power resources than IMD 14. As such, the pre-compensation techniques described in this disclosure should not be limited to being performed within external devices.

IMD 14 may be any of a variety of medical devices that provide therapy to patient 12, sense physiological or biological conditions of patient 12 or a combination thereof. In some instances, IMD 14 may be a device that provides electrical stimulation therapy in the form of cardiac rhythm management therapy to a heart of patient 12. In such a case, IMD 14 may include one or more implantable leads (not shown) that extend from IMD 14 and include one or more electrodes for delivering therapy to and/or sensing physiological signals of a heart of patient 12. The leads may be implanted within one or more atria or ventricles of the heart of patient 12 or a combination thereof. In other words, IMD 14 may be used for single chamber or multi-chamber cardiac rhythm management therapy. The cardiac rhythm management therapy delivered by IMD 14 may include, for example, pacing, cardioversion, defibrillation and/or cardiac resynchronization therapy (CRT).

In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like to treat various conditions, including movement and affective disorders such as chronic pain, Parkinson's disease, tremor and dystonia, urinary storage and voiding dysfunction, digestion dysfunction, sexual dysfunction or the like.

In further instances, IMD 14 may be a device that delivers a drug or therapeutic agent to patient 12 via an implantable catheter (not shown). IMD 14 may, for example, be implanted within a subcutaneous pocket in an abdomen of patient 12 and the catheter may extend from IMD 14 into the stomach, pelvic floor, brain, intrathecal space of the spine of patient 12 or other location depending on the application. IMD 14 may deliver the drug or therapeutic agent via the catheter to reduce or eliminate the condition of the patient and/or one or more symptoms of the condition of the patient. For example, IMD 14 may deliver morphine or ziconotide to reduce or eliminate pain, baclofen to reduce or eliminate spasticity, chemotherapy to treat cancer, or any other drug or therapeutic agent to treat any other condition and/or symptom of a condition.

In another instance IMD 14 may be a wireless (or leadless) sensor implanted within patient 12 to sense one or more physiological signals of patient 12. IMD 14 may be implanted at targeted monitoring sites and transmit the sensed signals, thus avoiding limitations associated with lead-based sensors.

External device 16 may be a programming device or monitoring device that allows a user, e.g., physician, clinician, technician or patient, to configure a therapy delivered by IMD 14 or to retrieve data sensed by IMD 14 or both. External device 16 may include a user interface that receives input from the user and/or displays data to the user, thus allowing the user to enter input to use in programming the therapy delivered by IMD 14 or display data retrieved from IMD 14. External device 16 may be a dedicated hardware device with dedicated software for programming or otherwise communicating with IMD 14. Alternatively, external device 16 may be an off-the-shelf computing device running an application that enables external device 16 to program or otherwise communicate with IMD 14. In some examples, external device 16 may be a handheld computing device that may be attached to or otherwise carried by patient 12. Alternatively, external device 16 may be a computer workstation, such as a CareLink® monitor, available from Medtronic, Inc. of Minneapolis, Minn.

IMD 14 and external device 18 may communicate with one another by any of a number of wireless communication techniques. Example wireless communication techniques include RF telemetry, but other techniques are also contemplated. In one instance, IMD 14 and external device 16 may communicate in accordance with the MICS band regulation and/or the MEDS band regulation. The MICS band regulation defines communication requirements for the 402-405 MHz frequency band. In accordance with the MICS band regulations, the frequency band is divided into ten channels with each channel corresponding to a 300 kilohertz (kHz) sub-band. The MEDS frequency band regulation defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band. IMD 14 and external device 16 may communicate using other frequency bands instead of or in addition to the MICS and MEDS bands, such as the industrial, scientific and medical (ISM) frequency bands.

As will be described in further detail with respect to FIG. 3, a transceiver of IMD 14 includes one or more receiver components that have undesired electrical responses, such as nonlinear phase response, sloped (or non-flat) amplitude response or both. In accordance with the techniques described in this disclosure, external device 16 filters signals to be transmitted to IMD 14 to compensate for distortions introduced by the undesired electrical responses (e.g., nonlinear phase response, sloped amplitude response or both) of one or more of the receiver components of IMD 14. For example, external device 16 may apply a filter to compensate for distortions introduced by band pass channel filters of the transceiver of IMD 14 that are used for channel selection. In this manner, at least a portion of the burden of digital processing to compensate for undesired electrical responses of the receiver components is shifted from IMD 14 to external device 16, which is better equipped to perform such heavy computationally complex functions, thereby reducing power consumption in IMD 14. In some instances, however, digital processing to compensate for undesired electrical responses of the receiver components may be distributed between IMD 14 to external device 16 such that each of them performs a portion of the compensation. In this case, external device 16 performs pre-compensation and IMD 14 performs post-compensation to fix distortions not accounted for in the pre-compensation of external device 16.

Figure 2:
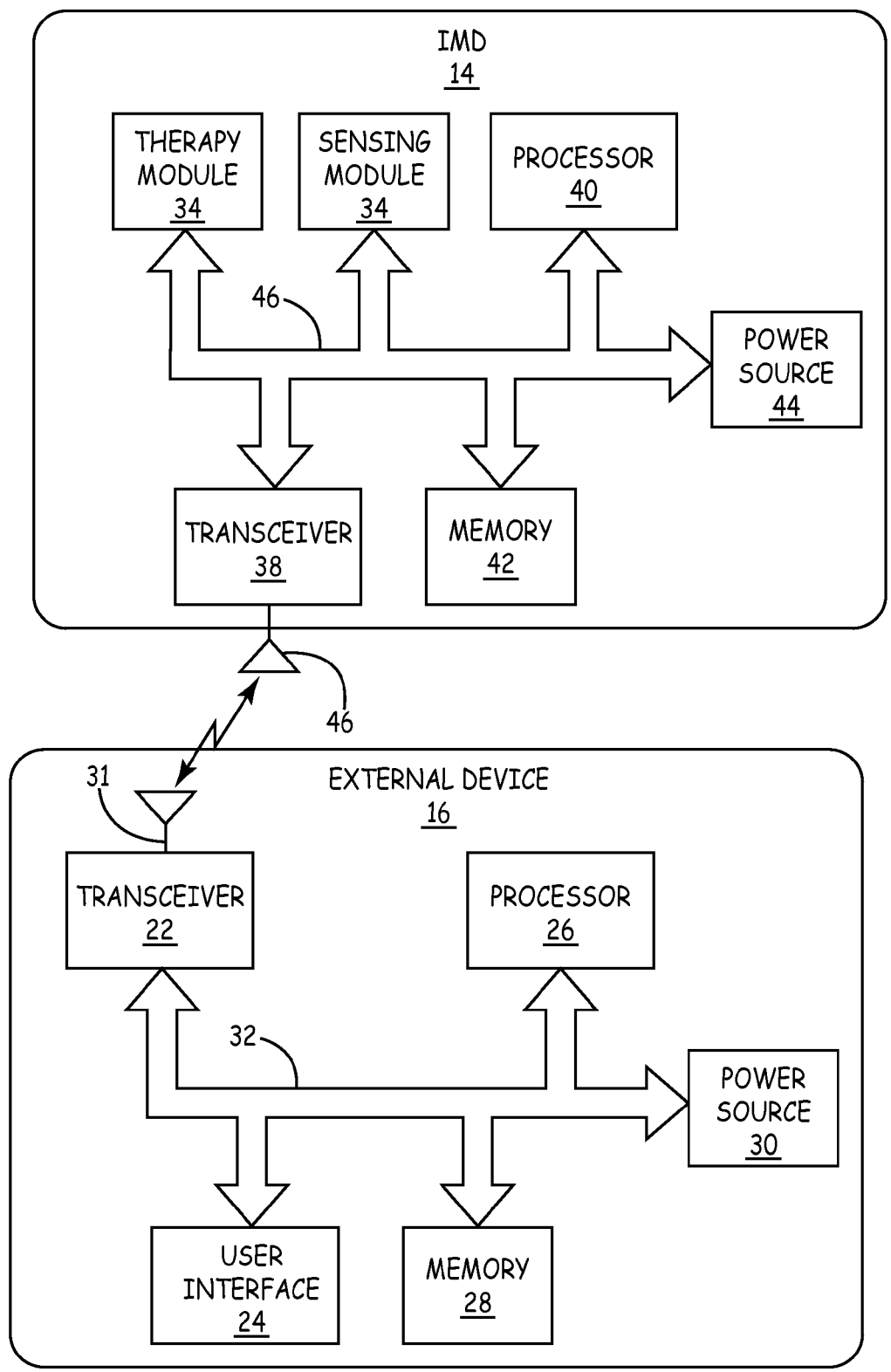
FIG. 2 is a block diagram illustrating the IMD and external device in further detail.

FIG. 2 is a block diagram illustrating IMD 14 and external device 16 in further detail. As illustrated in the example of FIG. 2, external device 16 includes a transceiver 22, user interface 24, processor 26, memory 28 and power source 30, all of which are interconnected by a data bus 32. IMD 14 includes a therapy module 34, sensing module 36, transceiver 38, processor 40, memory 42 and power source 44, all of which are interconnected by a data bus 46.

Power source 44 may include a rechargeable or non-rechargeable battery. A non-rechargeable battery may be selected to last for several years, while a rechargeable battery may be charged from an external charging device on a daily or weekly basis. In either case, and especially in the case of the non-rechargeable battery, the amount of power of the battery is limited. As such, it is desirable to reduce the amount of power drained from power source 44 as much as possible.

IMD 14 may obtain one or more sensed physiological or biological signals and detect one or more conditions of patient 12 from the sensed signals. Sensing module 36 is configured to monitor one or more physiological signals using one or more sensors connected to sensing module 36. In one example, sensing module 36 is configured to monitor signals sensed by one or more of electrodes on leads extending from IMD 14. In another example, sensing module 36 may be configured to monitor signals sensed by one or more sensors within or on IMD 14. In a further example, sensing module 36 may be configured to receive telemetry communications including signals sensed by one or more wireless or lead-less sensors and transmitted wirelessly to IMD 14. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter.

Sensing module 36 may store the sensed signals in memory 42. In some instances, sensing module 36 may store the sensed signals in raw form. In other instances, sensing module 36 may process the sensed signals and store the processed signals in memory 42. For example, sensing module 36 may amplify and filter the sensed signal and store the filtered signal in memory 42. The signals stored by sensing module 36 may, in some cases, be retrieved and further processed by processor 40.

IMD 14 may also provide therapy, such as electrical stimulation therapy or drug delivery therapy, to patient 12 in accordance with parameters of one or more selected therapy programs. In particular, processor 40 controls therapy module 34 to deliver therapy to patient 12 according to one or more therapy programs, which may be received from external device 16 and stored in memory 42. In the case of electrical stimulation therapy, therapy module 34 may include a stimulation generator that generates and delivers electrical stimulation therapy, e.g., in the form of pulses or shocks. Processor 40 may control the stimulation generator to deliver electrical stimulation pulses with amplitudes, pulse widths, frequency, and/or electrode polarities specified by the one or more therapy programs. In the case of drug delivery therapy, therapy module 34 may include a pump that delivers a drug or therapeutic agent to patient 12. Processor 40 may control the pump to deliver the drug or therapeutic agent with the dosage and frequency (or rate) specified by the one or more therapy programs. In some instances, IMD 14 may not provide therapy to patient 12, but only monitors patient 12 as in the case of an implantable loop recorder. In such cases, IMD 14 may not include therapy module 34.

Processor 40 controls transceiver 38 to transmit communications to and/or receive communications from another medical device, such as external device 16. As such, transceiver 38 may include a transmitter and a receiver. Transceiver 38 may also transmit communications to and/or receive communications from other external and/or implanted medical devices. Processor 40 may provide the data to be transmitted to external device 16 and the control signals for transmit and receive circuitry within transceiver 38, e.g., via data bus 46. Transceiver 38 transmits the data to external device 16 in accordance with the control signals from processor 40. Transceiver 38 may provide data received from external device 16 to processor 40. Processor 40 may analyze the received data, store the received data within memory 42 and configure components of IMD 14 in accordance with the received data.

Transceiver 38 includes any suitable hardware, firmware, software or any combination thereof for communicating with another device, such as external device 16. For example, transceiver 38 may include appropriate modulation, demodulation, frequency conversion, filtering, amplifier or other components for transmission and reception of data, including radio frequency (RF) components. As described above, one or more of the components of transceiver 38 may have undesirable electrical responses that introduce distortion into a received signal. For example, the components may have non-linear phase responses, sloped (i.e., not flat) amplitude responses, or the like. Transceiver 38 is also coupled to an antenna 46 for transmitting and receiving signals.

A user may interact with external device 16 to program IMD 14 to provide therapy in accordance with a selected therapy program and/or view data retrieved from IMD 14. The user may, for example, interact with external device 16 via user interface 24 to select therapy programs (e.g., sets of stimulation parameters), generate new therapy programs and/or modify therapy programs through individual or global adjustments. User interface 24 may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 16 can additionally or alternatively include a peripheral pointing device, such as a mouse, via which a user may interact with the user interface. In some embodiments, the display of external device 16 may include a touch screen display, and a user may interact with external device 16 via the display.

Processor 26, which like processor 40 may be one or more microprocessors, one or more controllers, one or more DSPs, one or more ASICs, or one or more FPGAs, as well as other discrete or integrated logic circuitry, or a combination thereof, controls transceiver 22 to transmit the parameters of the one or more selected therapy programs to transceiver 38 of IMD 14. The parameters of the one or more selected therapy programs may be stored within memory 28, which may be any volatile or non-volatile memory, or directly input by the user via user interface 24. Transceiver 22, under the control of processor 26, may also receive data from transceiver 38 of IMD 14, which may include sensed physiological parameters, diagnosis generated based on the sensed physiological parameters, a log of delivered therapies, information regarding the amount of remaining battery power or the like. Processor 26 may store the retrieved data in memory 28 for later processing or transmission to another device, e.g., a remote server.

Transceiver 22 communicates wirelessly with IMD 14 and, more specifically, with transceiver 38 of IMD 14. Transceiver 38 is coupled to an antenna 31 for transmitting and receiving signals. Transceiver 22, like transceiver 38 of IMD 14, may include a transmitter and receiver that include any suitable hardware, firmware, software or any combination thereof for communicating with IMD 14. For example, transceiver 22 may include appropriate modulation, demodulation, frequency conversion, filtering, amplifier or other components for transmission and reception of data, including RF components.

In accordance with the techniques described in this disclosure, external device 16 filters the signals to be transmitted to IMD 14 to pre-compensate for at least some of the distortion introduced by one or more of the components of the transceiver of IMD 14. The distortions may, for example, be due to a nonlinear phase response of the one or more components, a sloped amplitude response of the one or more components of transceiver 38 or the like. As such, transceiver 22 of external device 16 may include a compensation filter to pre-compensate for at least a portion of the undesirable electrical responses of the one or more components of transceiver 38 of IMD 14.

External device 16 may perform pre-compensation filtering using digital filters, such as digital finite impulse response (FIR) filters or infinite impulse response (IIR) filters. The complexity of the digital processing needed to implement these digital filters depends on the level of the nonlinear phase response or sloped amplitude response of the components of transceiver 38. In any case, shifting the digital processing necessary for compensating for the distortions introduced by the undesirable electrical responses of the components of IMD 14 to transceiver 22 of external device 16 reduces power consumption in IMD 14, in turn extending a service life of IMD 14 and/or power source 44. External device 16 is better equipped to perform such computationally complex functions due to the ability to easily recharge and/or replace power source 30 of external device 16. In fact, in some instances, power source 30 of external device 16 may be an AC power source, in which case, the amount of power available is unlimited. Power source 44, on the other hand, has a limited service life and may require a surgical procedure to replace.

Power source 30 of external device 16 delivers operating power to the components of external device 16. Power source 30 may include a battery and a power generation circuit to produce the operating power for the components of external device 16. In some examples, the battery may be rechargeable (e.g., nickel cadmium or lithium ion batteries) to allow extended operation. Recharging may be accomplished by electrically coupling power source 30 to a cradle or plug that is connected to an alternating current (AC) outlet. In addition or alternatively, recharging may be accomplished through proximal inductive interaction between an external charger and an inductive charging coil within external device 16. In other embodiments, non-rechargeable batteries (e.g., non-rechargeable lithium based batteries such as lithium iodide) may be used. In addition, external device 16 may be directly coupled to an AC outlet to power external device 16.

Processors 26 and 40 may include one or more of a microprocessor, a controller, a digital signal processor (DSP), an application specific integrated circuit (ASIC), a field-programmable gate array (FPGA), or equivalent discrete or integrated logic circuitry. The functions attributed to processors 26 and 40 herein may be embodied as software, firmware, hardware or any combination thereof. Memories 28 and 42 may include computer-readable instructions that, when executed by processors 26 and 40, respectively, cause external device 16 and IMD 14 to perform various functions attributed to external device 16 and IMD 14 herein. Memories 28 and 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), static random access memory (SRAM) or any other digital media.

Figure 3:
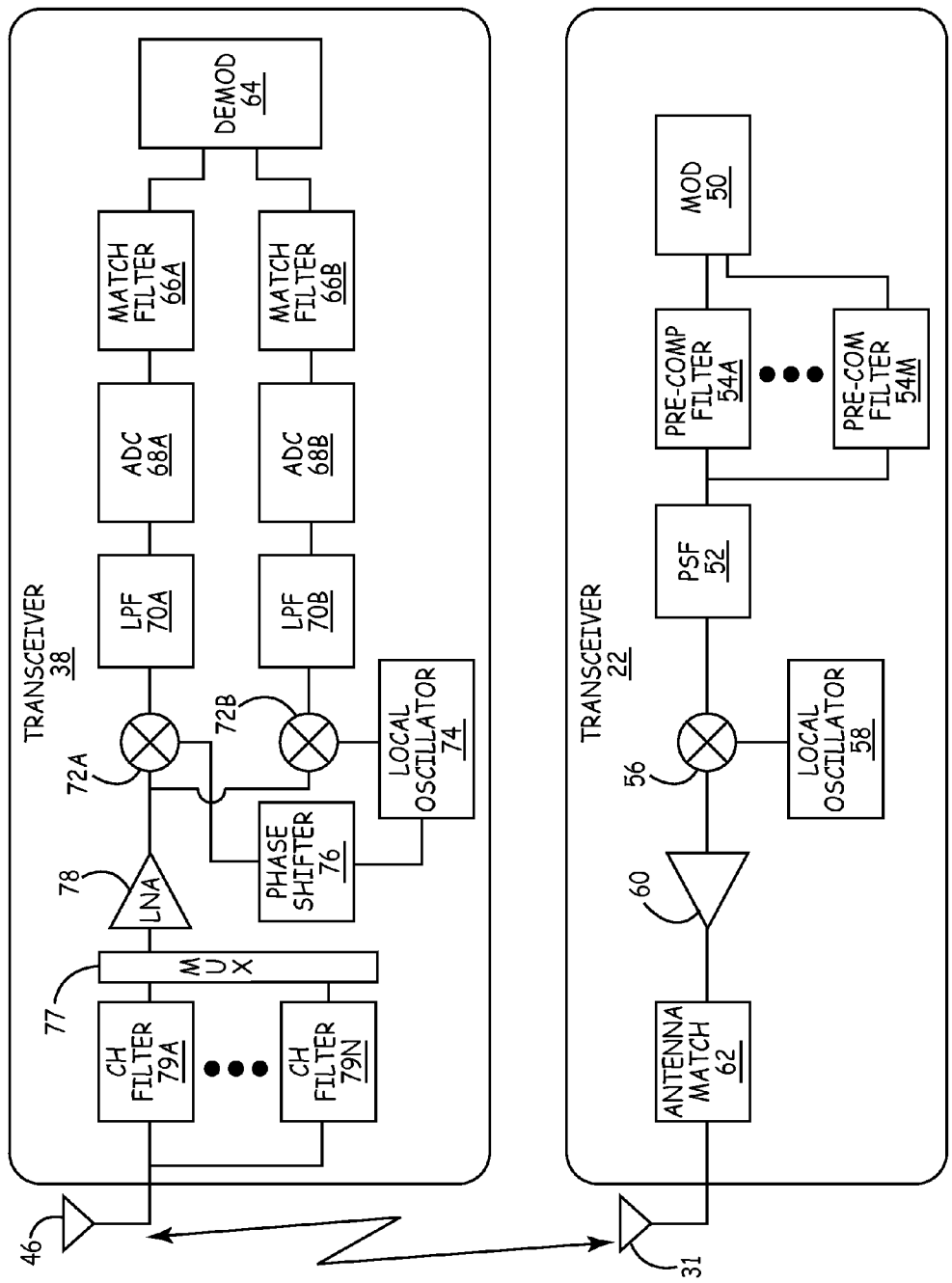
FIG. 3 is a block diagram illustrating example components of the transceivers of the IMD and external device in further detail.

FIG. 3 is a block diagram illustrating example components of transceivers 22 and 38 in further detail. In particular, FIG. 3 illustrates transmitter components of transceiver 22 of external device 16 and receiver components of transceiver 38 of IMD 14 for purposes of description. However, transceiver 38 of IMD 14 may also include transmitter components for transmitting signals from IMD 14 to external device 16. Likewise, transceiver 22 of external device 16 may include receiver components for receiving signals from IMD 14.

Transceiver 22 illustrated in FIG. 3 includes a modulator (MOD) 50, a pulse shaping filter (PSF) 52, one or more pre-compensation filters (PRE-COMP FILTER) 54A-54M, a mixer 56, a local oscillator 58, a power amplifier 60 and an antenna matching circuit 62. Transceiver 22 of FIG. 3 is one example transceiver and, in some instances, may include more or fewer components. Transceiver 38 illustrated in FIG. 3 includes a demodulator (DEMOD) 64, match filters 66A and 66B, analog to digital converters (ADCs) 68A and 68B, low pass filters (LPFs) 70A and 70B, mixers 72A and 72B, a local oscillator 74, a 90 degree phase shifter ($\pi/2$) 76, a multiplex switching network 77, a low noise amplifier (LNA) 78 and a band-pass channel filters 79A-79N (referred to herein as "channel filters 79").

As described above, transceiver 38 of IMD 14 receives signals transmitted from transceiver 22 of external device 16, such as signals requesting stored data, providing operating parameters or the like. Signals induced on antenna 46 are provided to each of channel filters 79. Each of channel filters 79 is tuned to an individual channel of the frequency band used for communication. When IMD 14 and external device 16 communicate using the MICS frequency band, for example, each of band-pass channel filters 79 is tuned to one of the ten 300 kHz channels in the 402-405 MHz frequency band. In this case, N is equal to 10, i.e., transceiver 38 has ten channel filters 79. As another example, each of channel filters 79 may be tuned to one of the twenty 100 kHz channels located in the MEDS frequency band. In this case, N is equal to 20, i.e., transceiver 38 has twenty channel filters 79. Transceiver 38 may include any number of band pass channel filters 79 depending on the number of available channels of the one or more frequency bands used for communication.

In instances in which a plurality of channel switch filters 79 are used, a multiplexing switching network 77 may be used to select which of the channel switch filters 79 to couple to the antenna 46 and/or LNA 78. In other instances, the plurality of channel switch filters 79 may actually be implemented using a single filter that is tunable, e.g., using a bias voltage. In any case, the output of appropriate one of channel filters 79 is provided to an amplifier, e.g., LNA 78. LNA 78 may have a low inherent noise floor and amplifies the desired telemetry signal. The output of LNA 78 is coupled to mixers 72A and 72B. The receive path splits into two parallel paths between LNA 78 and demodulator 64. One of the parallel paths (e.g., the top receive path that includes mixer 72A, low pass filter 70A, ADC 72A and match filter 66A) generates an INPHASE signal and the other one of the parallel paths (e.g., the bottom receive path that includes mixer 72B, low pass filter 70B, ADC 72B and match filter 66B) generates a QUADRATURE signal.

In the INPHASE receive path, mixer 72A mixes the output of LNA 78 with a phase shifted version of an intermediate frequency signal generated by local oscillator 74. In particular, the output of local oscillator 74 is phase shifted by $-\pi/2$ or $-90$ degrees by block 76 and provided to mixer 72A. The output of mixer 72A passes through LPF 70A. The output of LPF 70A is provided to ADC 68A which converts the analog signal to a digital signal. The digital signal output by ADC 68A is provided to matched filter 66A.

Similarly, in the QUADRATURE receive path, mixer 72B mixes the output of LNA 78 with the intermediate frequency signal generated by local oscillator 74. The output of mixer 72B, i.e., the QUADRATURE signal, is 90 degrees out of phase with the INPHASE signal output from mixer 72A. The output of mixer 72B passes through LPF 70B. The output of LPF 70B is provided to ADC 68B which converts the analog signal to a digital signal. The digital signal output by ADC 68B is provided to matched filter 66B. The QUADRATURE and INPHASE signals output of matched filters 66A and 66B are provided to demodulator 64, which demodulates the signals to obtain the information sent via the carrier wave. Demodulator 64 outputs the demodulated data to processor 40 (FIG. 2) for decoding and/or further processing.

In one embodiment, channel filters 79 may be RF microelectromechanical systems (MEMS) filters. The RF MEMS filters may be implemented on the same chip as the other transceiver components, thus reducing the footprint of the transceiver components. Moreover, as described above, the RF MEMS filters are narrow-band, i.e., tuned to a band corresponding to a particular channel within the frequency band used for communication. Tuning the RF MEMS filters to particular channels within the frequency band allows for filtering of received RF signals before providing the signal to the transceivers front end circuitry, e.g., LNA 78, mixers 72, LPFs 70, ADCs 68 and the like. Conventionally, this filtering occurred at an intermediate frequency or baseband frequency, thus requiring the front-end components to have a larger dynamic range due to the large separation between the energy levels of the desired signal and the undesired signal. Using RF MEMS filters to filter the signals prior to providing them to the front-end components allows for front-end components with a lower complexity, thus reducing the transceiver's area and power consumption while still providing effective filtering of undesired signals. Although described in the context of RF MEMS filters, other types of filters may be used to filter the signals at RF.

Although RF MEMS filters have several advantages, such as size, the electrical response of the RF MEMS filters may be somewhat undesirable. The RF MEMS filters may, for example, exhibit non-linear phase responses and/or sloped amplitude response, which introduce distortions into the received signal. Conventional filters, such as SAW filters, have a substantially linear phase response and a substantially constant magnitude frequency response. As such, the advantages provided by the RF MEMS filters may be offset by the need to correct distortions introduced into the signal by the undesirable electrical response of the RF MEMS filters.

The distortion introduced into the received signal due to undesirable phase response and/or amplitude response can be compensated for through the use of digital processing techniques, such as digital finite impulse response (FIR) filters or infinite impulse response (IIR) filters. A FIR filter is a digital structure which multiplies, in parallel, time-delayed samples of an incoming waveform by pre-calculated coefficients, and then computes the sum of those parallel products. The number of parallel computations is related to the level of non-linearity of the undesired phase response and/or magnitude frequency response. RF MEMS filters may, in some instances, have a high level of non-linear phase response. As such, IMD 14 may be required to expend significant resources and power to correct the distortion caused by use of the RF MEMS filters.

In accordance with the techniques of this disclosure, however, at least some of the digital processing burden is shifted from IMD 14 to external device 16, which is better suited to expend the processing and power resources. In particular, transceiver 22 of external device 16 pre-processes the signal to be sent to IMD 14 to account for at least a portion, and in some instances all, of the distortion caused by the undesired phase response and/or amplitude response of the components of transceiver 38 of IMD 14. This reduces, and in some instances eliminates, the need for post-processing the signal within IMD 14 to account for the electrical responses of the components.

Data to be transmitted to IMD 14 is provided to modulator 50 of transceiver 22. Modulator 22 modulates the data in accordance with any of a variety of modulation techniques. Modulator 22 may, for example, modulate the data using any analog or digital modulation techniques, including, but not limited to, quadrature amplitude modulation (QAM), phase shift keying (PSK), frequency shift keying (FSK), amplitude shift keying (ASK), or other technique and/or combination of techniques.

Transceiver 22 of external device 16 filters the modulated signal using one of pre-compensation filters 54A-54M to pre-compensate for the undesired electrical responses of one or more components of transceiver 38 of IMD 14. In one example, compensation filters 54A-54M may each pre-compensate for the undesired electrical responses of respective ones of channel filters 79A-79N. In other words, the pre-compensation that is performed by transceiver 22 may be different for each channel. In this case, the value of M is equal to N. In another example, transceiver 22 of external device 16 may include only a single compensation filter instead of a plurality of compensation filters as described in further detail with respect to FIG. 4. In this case, the same compensation filter may be used for pre-compensation regardless of the channel on which the signal will be transmitted.

Compensation filters 54A-54M may also pre-compensate for one or more other components of transceiver 38 instead of or in addition to the channel filters 79A-79N. For example, compensation filters 54A-54M may pre-compensate for non-linear phase responses or sloped amplitude responses in LNA 78, LPFs 70A and 70B, ADCs 68A and 68B, or other components within the receive path of transceiver 38. In this manner, the techniques described in this disclosure leverage pre-compensation for the purpose of shifting a static computational burden from one end of the communication link (i.e., from IMD 14) to the other end (i.e., external device 16).

Additionally, compensation filters 54A-54M may pre-compensate for undesired electrical responses of one or more components of transceiver 22 of external device 16 that will process the signal prior to transmitting it to IMD 14, e.g., mixer 56, amplifier 60 or antenna match circuit 62.

Compensation filters 54A-54M may, in one instance, be digital FIR filters or IIR filters. As described above, FIR filters are digital structures which multiply, in parallel, time-delayed samples of an incoming waveform by pre-calculated coefficients, and then compute the sum of those parallel products. The number of parallel computations is related to the level of the undesired phase response and/or magnitude frequency response of the components for which the pre-compensation is performed. In other words, the transmitted waveform is put through a filter whose impulse response is such that its convolution with the impulse response of the one or more components of IMD 14 (e.g., channel filters 79 or other component in the receive path) gives a delayed delta function.

The signal to be transmitted is also filtered using pulse shaping filter 52 to make the signal better suited to the communication channel over which it will be transmitted. Pulse shaping filter 52 essentially limits the effective bandwidth of the signal to reduce the likelihood of intersymbol interference by the channel. As such, the pulse shaping filter 52 ensures that the signal fits in the frequency band of the channel over which it is transmitted. Pulse shaping filter 52 may be any of a number of pulse shaping filters, including, but not limited to, a raised cosine filter, a sinc shaped filter, a Gaussian filter or a boxcar filter. In one example, pulse shaping filter 52 may be a separate digital filter, e.g., FIR filter, that is applied to the signal. In another example, pulse shaping filter 52 and pre-compensation filters 79 may be implemented using a single FIR filter.

The pre-compensated, pulse-shaped signal is input to mixer 56, which mixes the signal with a signal from local oscillator 58 to convert the signal to a different frequency, e.g., from baseband to RF. The mixed signal is amplified by amplifier 60 and sent through antenna matching circuit 62 to antenna 31 for transmission. Antenna matching circuit 62 matches the impedance of amplifier 60 with the impedance of antenna 31.

Figure 4:
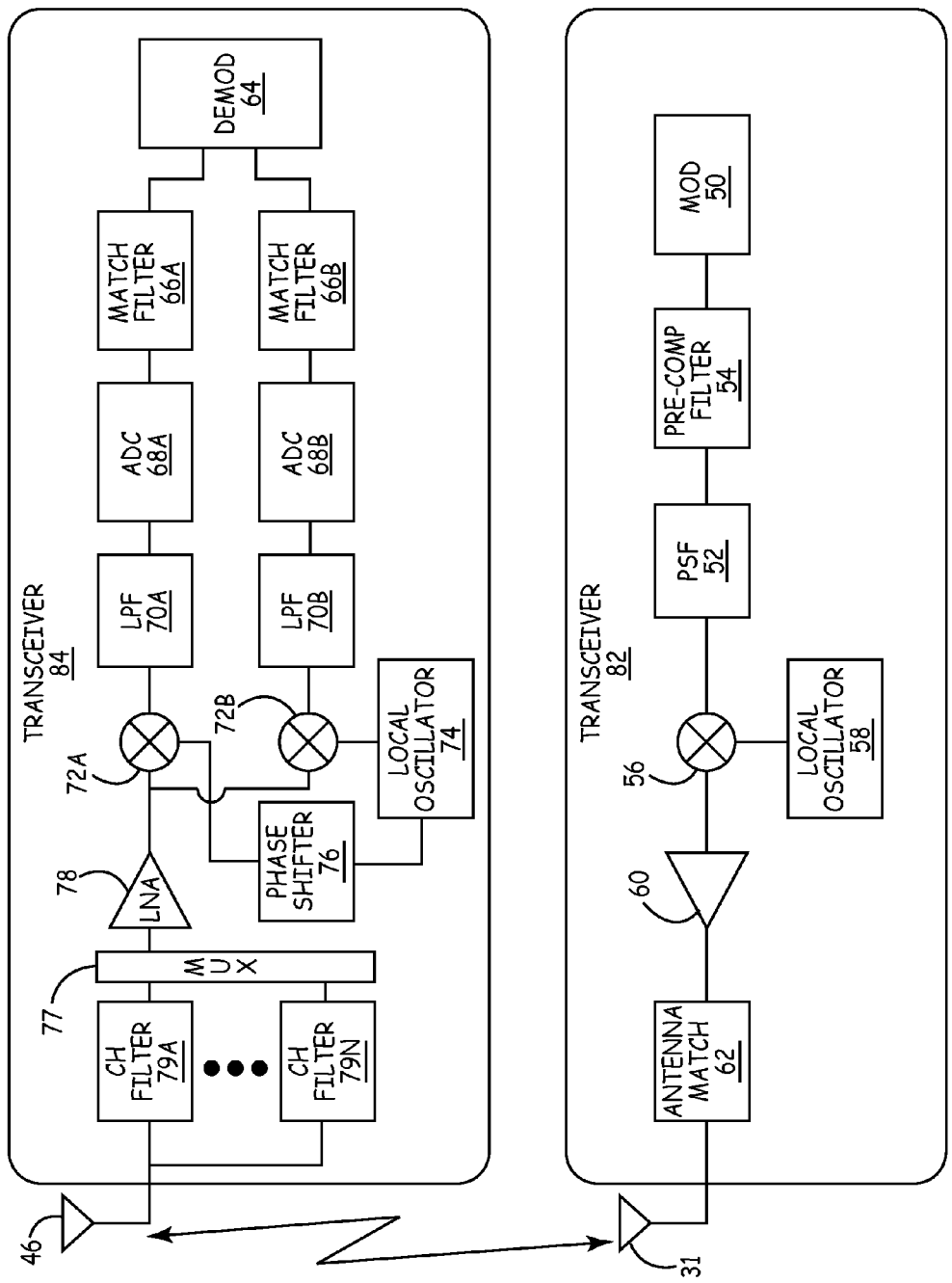
FIG. 4 is a block diagram illustrating another example set of components of the transceivers of the IMD and external device in further detail.

FIG. 4 is a block diagram illustrating another example set of components of transceivers 82 and 84 in further detail. Transceivers 82 and 84 of FIG. 4 conform substantially with transceivers 22 and 38 of FIG. 3, respectively. However, transceiver 82 of FIG. 4 includes only a single pre-compensation filter 54 instead of a plurality of compensation filters as in transceiver 22 of FIG. 3. As such, transceiver 82 applies pre-compensation filter 54 to pre-compensate for the undesired electrical response of the component(s) of transceiver 84 regardless of the channel on which the signal will be transmitted.

Figure 5:
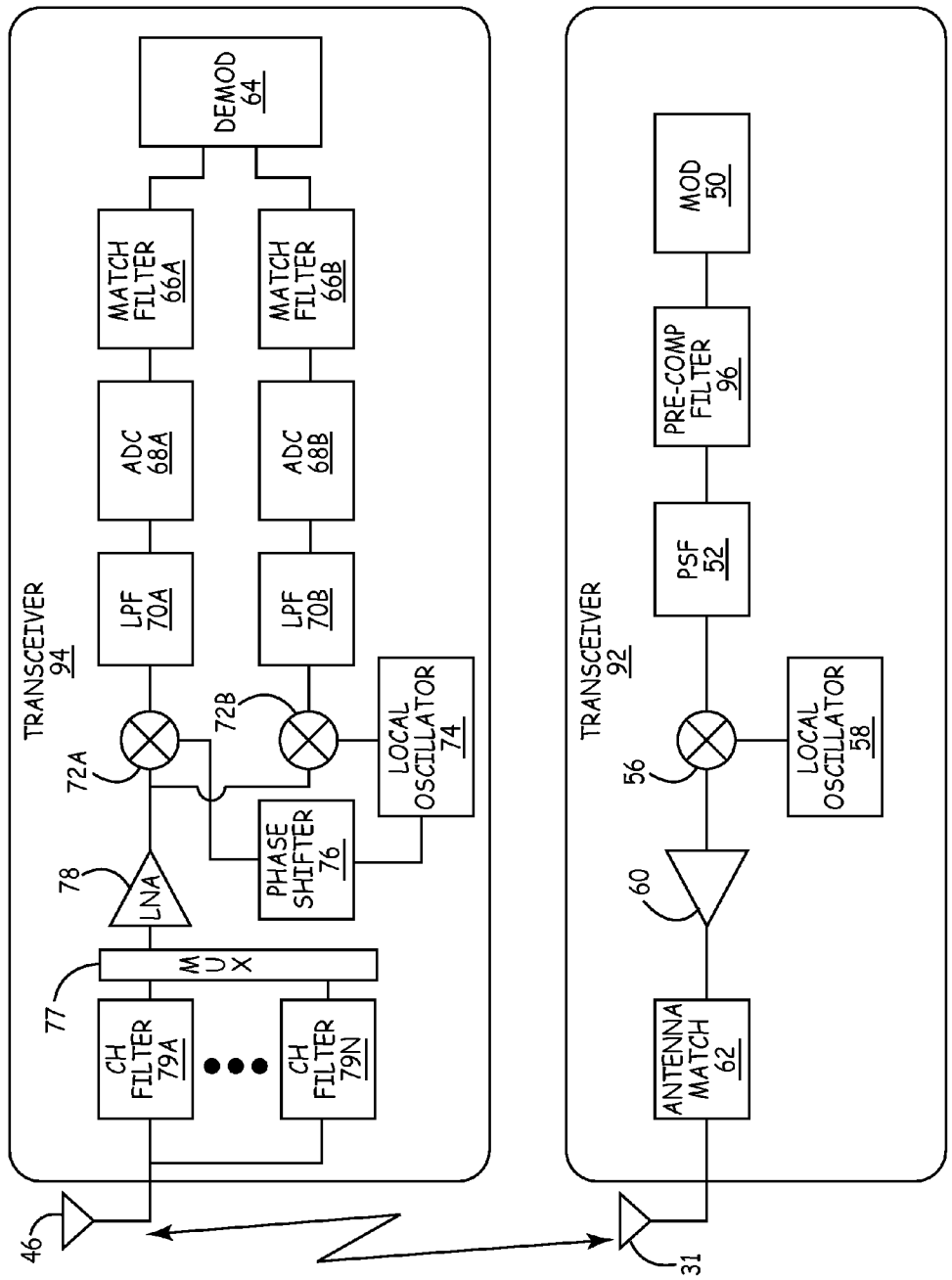
FIG. 5 is a block diagram illustrating a further example set of components of the transceivers of the IMD and external device in further detail.

FIG. 5 is a block diagram illustrating another example set of components of transceivers 92 and 94 in further detail. Transceivers 92 and 94 of FIG. 5 conform substantially with transceivers 82 and 84 of FIG. 4, respectively. However, transceiver 94 of FIG. 5 includes compensation filters 66A and 66B that post-compensate for at least a portion of the distortions in the received signal caused by undesirable electrical responses that are not accounted for by the pre-compensation performed by transceiver 92 of external device 16. In other words, FIG. 5 illustrates an example in which the processing required for compensation of the undesired electrical responses of the one or more components of transceiver 94 are distributed between IMD 14 and external device 16.

Figure 6:
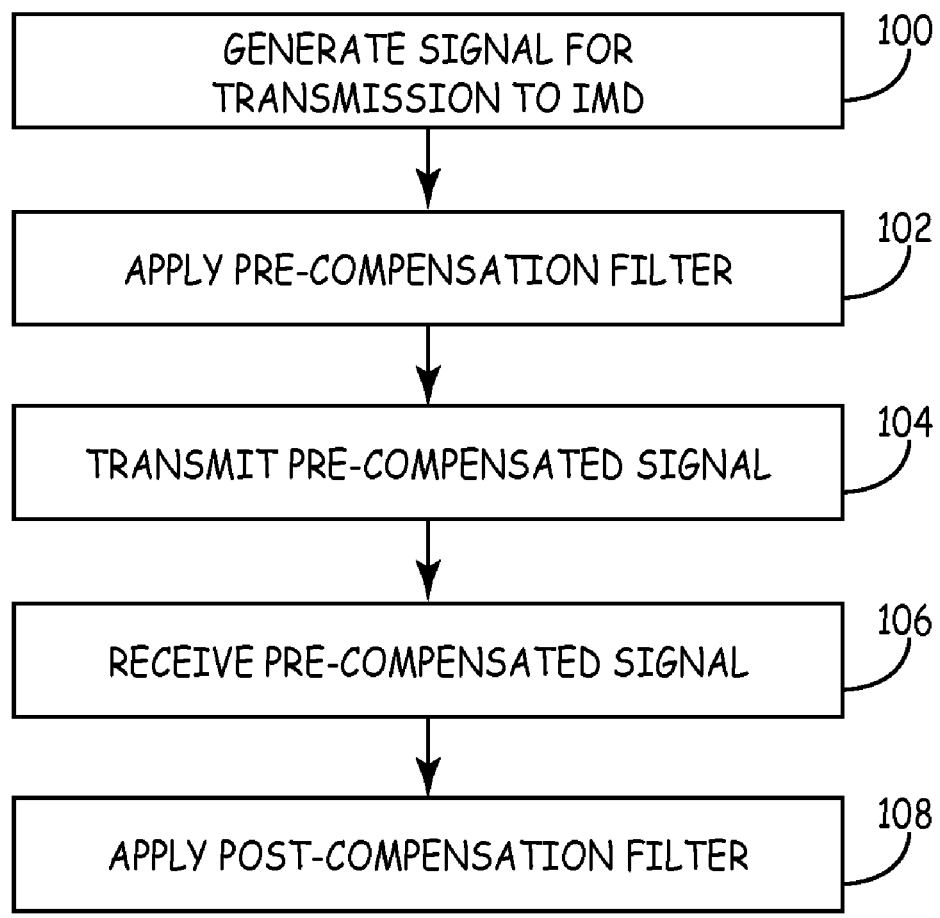
FIG. 6 is a flow diagram illustrating the techniques of this disclosure.

FIG. 6 is a flow diagram illustrating the techniques of this disclosure. Initially, external device 16 generates a signal for transmission to IMD 14 (100). Transceiver 22 of external device 16 applies a pre-compensation filter 54 to pre-compensate for the undesired electrical responses of one or more receiver components of IMD 14 (102). As described in detail above, transceiver 22 may select one of a plurality of pre-compensation filters to apply based on the channel over which the signal is to be transmitted or apply the same pre-compensation filter to each of the signals regardless of channel. In this manner, transceiver 22 pre-processes the signal to be sent to IMD 14 to account for at least a portion, and in some instances all, of the distortion caused by the undesired electrical response, e.g., phase response and/or amplitude response, of the receiver components of IMD 14. Transceiver 22 transmits the pre-compensated signal via antenna 31 (104).

Transceiver 38 of IMD 14 receives the pre-compensated signal via antenna 46 (106). After processing the received signal with the receiver components, transceiver 38 may, in some instances, apply a post-compensation filter 66 (108). Post-compensation filter 66 compensates for the portion of the distortions in the received signal caused by undesirable electrical responses that are not accounted for by the pre-compensation performed by transceiver 38 of external device 16. In such a case, the processing demands for compensation of the undesired electrical responses of the one or more components of transceiver 38 may be viewed as being distributed between IMD 14 and external device 16. In other instances, however, the entire compensation burden may be shifted to external device 16 in which case no post-compensation filtering may be necessary, at least to correct distortion from the electrical response of the receiver components.

The techniques described in this disclosure may be implemented, at least in part, in hardware, software, firmware or any combination thereof For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A system comprising:
an implantable medical device comprising at least one receiver component that has an undesired electrical response, wherein the implantable medical device includes a plurality of band pass channel filters each of which corresponds with a respective one of a plurality of channels of a frequency band; and
an external device that transmits signals to the implantable medical device, wherein the external device maintains a plurality of pre-compensation filters each of which pre-compensates for the undesired electrical response of a respective one of the plurality of band pass channel filters, and the external device selects one of the plurality of pre-compensation filters to apply to the signals based on the one of the plurality of channels selected for transmitting the signal and applies the selected one of the plurality of pre-compensation filters to the signals prior to transmission of the signals to pre-compensate for at least a portion of an undesired electrical response of the at least one receiver component of the implantable medical device.

2. The system of claim 1, wherein the band pass channel filters comprises radio frequency (RF) microelectromechanical systems (MEMS) filters.

3. The system of claim 1, wherein the implantable medical device further comprises at least one post-compensation filter that is applied to the signals received from the external device to compensate for the portion of the undesired electrical response of the at least one receiver component not accounted for in the pre-compensation.

4. The system of claim 1, wherein the pre-compensation filter of the external device pre-compensates for undesired electrical responses of at least two receiver components of the implantable medical device.

5. The system of claim 1, wherein the pre-compensation filter of the external device pre-compensates for one of a nonlinear phase response and a sloped amplitude response of the at least one receiver components of the implantable medical device.

6. The system of claim 1, wherein the pre-compensation filter pre-compensates for nonlinearities of a channel on which the signal is to be transmitted in addition to the undesired electrical response of the at least one receiver component.

7. The system of claim 1, wherein the pre-compensation filter comprises one of a finite impulse response (FIR) filter and an infinite impulse response (IIR) filter.

* * * * *